United States Patent
Kreis

(10) Patent No.: US 8,592,595 B2
(45) Date of Patent: Nov. 26, 2013

(54) PREPARATION OF (N-HETEROCYCLYL) ARYL ETHERS

(75) Inventor: Michael Kreis, Leverkusen (DE)

(73) Assignee: Saltigo GmbH, Leverkusen (DE)

( * ) Notice: Subject to any disclaimer, the term of this patent is extended or adjusted under 35 U.S.C. 154(b) by 983 days.

(21) Appl. No.: 12/579,583

(22) Filed: Oct. 15, 2009

(65) Prior Publication Data

US 2010/0152454 A1    Jun. 17, 2010

(30) Foreign Application Priority Data

Oct. 25, 2008  (DE) .......................... 10 2008 053 240

(51) Int. Cl.
*C07D 211/02*    (2006.01)

(52) U.S. Cl.
USPC ....................................................... 546/185

(58) Field of Classification Search
USPC ........................................................ 546/185
See application file for complete search history.

(56) References Cited

FOREIGN PATENT DOCUMENTS

| | | |
|---|---|---|
| DE | 292456 | 6/1916 |
| EP | 1947098 | 7/2008 |
| WO | WO97/23216 | 7/1997 |
| WO | WO02/072621 | 9/2002 |
| WO | WO2005092832 | 10/2005 |
| WO | WO2008/140090 | 11/2008 |

OTHER PUBLICATIONS

European Search Report from co-pending Application EP09173002 dated Jan. 18, 2010, 5 pages.
Barta-Szalai, G., et al.; "Oxamides as novel NR2B selective NMDA receptor antagonists"; Bioorganic & Medicinal Chemistry Letters, Pergamon, Elsevier Science, GB Bd. 14, Jan. 1, 2004, pp. 3953-3956.

*Primary Examiner* — John Mabry
(74) *Attorney, Agent, or Firm* — Michael A. Miller

(57) ABSTRACT

The present invention relates to a process for the preparation of optionally substituted (N-heterocyclyl) aryl ethers.

14 Claims, No Drawings

PREPARATION OF (N-HETEROCYCLYL) ARYL ETHERS

BACKGROUND OF THE INVENTION

The present invention relates to a process for the preparation of optionally substituted (N-heterocyclyl) aryl ethers.

Various (N-heterocyclyl) aryl ethers are already of importance as intermediates for the synthesis of medicaments and agrochemicals and are an essential structural element in active ingredients against e.g. infectious diseases, schizophrenia, depression, neurodegenerative diseases and also in pesticide intermediates.

Various processes for the preparation of (N-heterocyclyl) aryl ethers are known.

Thus, for example, WO 2005/092832 describes the preparation of (N-heterocyclyl) aryl ethers, in particular of an aryl piperidinyl ether, starting from N-boc-4-hydroxypiperidinol via a complex three-stage synthesis. The same is true for WO 97/23216.

Alternatively to this, in EP 1947098 A1, the synthesis takes places starting from N-benzyl-4-hydroxypiperidinol with the introduction of a protective group and reaction with 4-trifluoromethyl-fluorobenzene, which has considerable disadvantages in the economic feasibility.

The preparation of an (N-heterocyclyl) aryl ether is described in WO 2002/072621 starting from N-boc-4-hydroxypiperidinol via a Mitsunobu reaction using diethyl azocarboxylate (DEAD). This route is difficult to realize on account of the explosivity of the DEAD used, especially on an industrial scale.

The known processes have the disadvantages that they are either uneconomical, ecologically unacceptable or problematic from a safety aspect.

It was therefore the object to provide a process which does not have the disadvantages of the processes hitherto and produces the (N-heterocyclyl) aryl ethers in good yields, in a cost-effective manner on an industrial scale.

SUMMARY OF THE INVENTION

Surprisingly, it has been found that with the process according to the invention, using transition metal catalysts and special solvents, in particular carboxylic acids, it was possible to overcome the disadvantages of the prior art and to prepare (N-heterocyclyl) aryl ethers in good yields.

The invention therefore provides a process for the preparation of compounds of the formula (I)

characterized in that compounds of the formula (II)

are reacted in the presence of at least one transition metal catalyst,
at least one organic polar solvent
and hydrogen,
where CYCLYL-N is an optionally substituted 5- to 8-membered, cyclic saturated or partially unsaturated, non-aromatic N-heterocyclic radical having up to two nitrogen atoms which is linked via a ring carbon atom to the oxygen atom of the [$R^2$—O] radical, and ARYL-N is an optionally substituted N-heterocyclic 5- to 8-membered aromatic radical having up to two nitrogen atoms which is linked via a ring carbon atom of the aromatic radical to the oxygen atom of the [$R^2$—O] radical, $R^2$ is an optionally substituted $C_6$-$C_{20}$-aryl and
$R^1$ is bonded to a nitrogen atom of the CYCLYL-N and is hydrogen or —C(=O)(R) and R is $C_1$-$C_{15}$-alkyl, particularly preferably $C_1$-$C_6$-alkyl, $C_1$-$C_8$-alkylthio, $C_1$-$C_8$-alkoxy, $C_6$-$C_{24}$-aryl, $C_8$-$C_{26}$-arylalkyl, $C_1$-$C_8$-haloalkyl, $C_1$-$C_8$-haloalkoxy, $C_1$-$C_8$-haloalkylthio, where halogen=F, Cl, Br, 5- to 8-membered saturated heterocyclyl where hetero=(oxygen, sulphur, or nitrogen), hydrogen or $C_1$-$C_8$-mono- or $C_1$-$C_{16}$-dialkylamino, which may optionally be further substituted;

R is particularly preferably $C_1$-$C_6$-alkyl or hydrogen.

Within the context of the invention, alkyl or alkoxy is a straight-chain, cyclic, branched or unbranched alkyl or alkoxy radical having 1 to 15 ($C_1$-$C_{15}$), preferably 1 to 12 ($C_1$-$C_{12}$), particularly preferably 1 to 6 ($C_1$-$C_6$) and very particularly preferably having 3 to 6 ($C_3$-$C_6$) carbon atoms.

By way of example and preferably, alkyl is methyl, ethyl, n-propyl, isopropyl, n-, iso, s- or t-butyl, cyclopropyl, cyclobutyl, cyclopentyl, cyclohexyl, cycloheptyl, n-pentyl, 1-methylbutyl, 2-methylbutyl, 3-methylbutyl, neopentyl, 1-ethylpropyl, cyclohexyl, cyclopentyl, n-hexyl, n-heptyl, n-octyl, n-decyl and n-dodecyl and alkoxy is methoxy, ethoxy, n-propoxy, isopropoxy, t-butoxy, n-pentoxy and n-hexoxy.

Preferably, $R^2$ is a $C_6$-$C_{20}$-aryl radical which is optionally substituted by alkyl, aryl, alkoxy, haloalkyl, haloalkylthio or haloalkyloxy where halogen=F, Cl and Br.

$R^2$ is particularly preferably a $C_6$-$C_{20}$-aryl radical which is optionally monosubstituted or polysubstituted by ($C_1$-$C_6$)-alkyl, ($C_1$-$C_6$)-alkoxy, ($C_1$-$C_7$)-perfluoroalkyl, ($C_1$-$C_7$)-perchloroalkyl, ($C_1$-$C_7$)-perfluoroalkoxy and ($C_1$-$C_7$)-perchloroalkoxy.

In a particularly preferred embodiment, $R^2$ is a $C_6$-$C_{20}$-aryl radical which is optionally monosubstituted or polysubstituted by trifluoromethoxy, methoxy and/or methyl. In a very particularly preferred embodiment, $R^2$ is 2-, 3- or 4-trifluoromethoxyphenyl, 2-, 3- or 4-methoxyphenyl or 2-, 3- or 4-phenylmethyl.

Within the context of the invention, aryl is a mono-, bi- or tricyclic carbocyclic aromatic radical having preferably 6 to 20 aromatic carbon atoms ($C_6$-$C_{20}$-aryl).

The carbocyclic aromatic radicals can be substituted by up to five identical or different substituents per cycle, such as e.g. alkyl, alkoxy, aryl, arylalkyl, carboxyl, dialkylamino, halogen, haloalkyl, haloalkoxy, haloalkylthio and monoalkylamino. By way of example and preferably, $C_6$-$C_{20}$-aryl is biphenyl, phenyl, naphthyl, phenanthrenyl, anthracenyl or fluorenyl.

Within the context of the invention, mono- or dialkylamino is an amino group with one or two identical or different, cyclic, straight-chain or branched alkyl substituents which preferably have in each case 1 to 10, particularly preferably 1 to 6 ($C_1$-$C_6$) carbon atoms.

By way of example and preferably, monoalkylamino is methylamino, ethylamino, n-propylamino, isopropylamino, t-butylamino, n-pentylamino and n-hexylamino and also dialkylamino for N,N-dimethylamino, N,N-diethylamino, N-ethyl-N-methylamino, N-methyl-N-n-propylamino, N-isopropyl-N-n-propylamino, N-t-butyl-N-methylamino, N-ethyl-N-n-pentylamino and N-n-hexyl-N-methylamino.

Arylalkyl is in each case independently of the others a straight-chain, cyclic, branched or unbranched alkyl radical according to the definition above which can be monosubstituted, polysubstituted or completely substituted by aryl radicals according to the definition above. One example of arylalkyl is benzyl. Preference is given to arylalkyls having 7 to 13 ($C_7$-$C_{13}$) carbon atoms, particular preference being given to arylalkyls having 7 to 10 ($C_7$-$C_{10}$) carbon atoms.

Within the context of the invention, halogens are preferably fluorine, chlorine and bromine, particularly preferably fluorine and chlorine.

Within the context of the invention, haloalkyl or haloalkoxy is a straight-chain, cyclic, branched or unbranched alkyl or alkoxy radical according to the definition above which is monosubstituted, polysubstituted or completely substituted by halogen atoms.

By way of example and preferably, haloalkyl is chloroethyl, chloropropyl, dichloromethyl, difluoromethyl, fluoromethyl, fluoroethyl, fluoropropyl and 2,2,2-trifluoroethyl and haloalkoxy is difluoromethoxy, fluoroethoxy, fluoromethoxy, trifluoromethoxy, trichloromethoxy and 2,2,2-trifluoroethoxy.

Haloalkyl and haloalkoxy include, for example, the perfluoroalkyl, perchloroalkyl and the perfluoroalkoxy and perchloroalkoxy radicals. Particular preference is given to perfluoroalkyl, perchloroalkyl and perfluoroalkoxy and perchloroalkoxy radicals having 1 to 5 ($C_1$-$C_5$) carbon atoms. Very particular preference is given to the perfluoroalkoxy and perchloroalkoxy radicals selected from the group trifluoromethyl, trichloromethyl, pentafluoroethyl, heptafluoroisopropyl and nonafluorobutyl.

In a further preferred embodiment, ARYL-N is pyridyl which is optionally monosubstituted or polysubstituted by alkoxy, alkyl, aryl, haloalkyl, haloalkylthio or haloalkyloxy where halogen=F, Cl and Br.

ARYL-N is particularly preferably pyridyl which is optionally monosubstituted or polysubstituted by ($C_1$-$C_6$)-alkyl, ($C_1$-$C_6$)-alkoxy, ($C_1$-$C_7$)-perfluoroalkyl, ($C_1$-$C_7$)-perchloroalkyl, ($C_1$-$C_7$)-perfluoroalkoxy and ($C_1$-$C_7$)-perchloroalkoxy.

Within the context of the invention, haloalkylthio is a straight-chain, cyclic, branched or unbranched radical having 1 to 15 carbon atoms, preferably having 1 to 7 ($C_1$-$C_7$) carbon atoms which is monosubstituted, polysubstituted or completely substituted by halogen atoms. By way of example and preferably, haloalkylthio is chloroethylthio, chlorobutylthio, chlorohexylthio, chloropentylthio, chlorododecylthio, dichloroethylthio, fluoroethylthio, trifluoromethylthio and 2,2,2-trifluoroethylthio.

In a very particularly preferred embodiment, ARYL-N is 2-, 3- or 4-trifluoromethoxypyridyl, 2-, 3- or 4-methoxypyridyl or 2-, 3- or 4-methylpyridyl.

Within the context of the invention, the N-heterocyclic 5- to 8-membered radical is preferably the radical of an aromatic and/or nonaromatic heterocycle having up to two nitrogen atoms, preferably one nitrogen atom which is linked via a ring carbon atom to the oxygen atom of the [$R^2$—O] radical. By way of example and particularly preferably the following may be mentioned: azepinyl, pyrrolyl, imidazolyl, pyridyl, pyrimidinyl, azepanyl, pyrrolidinyl, piperidinyl, piperazinyl and pyridazinyl.

Within the context of the invention, the 5- to 8-membered saturated heterocyclyl is preferably a heterocycle radical with up to 3 identical or different heteroatoms from the series S, N and/or O which is linked via a ring carbon atom, ring nitrogen atom, ring oxygen atom or ring sulphur atom. Preference is given to a 5- to 8-membered saturated heterocyclyl having up to 2 identical or different heteroatoms from the series S, N and/or O. By way of example, the following may be mentioned: azepanyl, pyrrolidinyl, piperidinyl, piperazinyl, morpholinyl or tetrahydrofuryl. Preference is given to azepanyl, pyrrolidin-1-yl, pyrrolidin-2-yl, pyrrolidin-3-yl, pyrrolidin-1-yl, piperidin-1-yl, piperidin-4-yl, piperazinyl, morpholinyl, tetrahydrofur-2-yl or tetrahydrofur-3-yl.

For example and preferably, the compounds of the formula (II) used are unsubstituted phenoxypyridines, 4-[4-$R^2$—O]-ARYL-N or 4-[2-$R^2$—O]-ARYL-N, i.e. in particular 4-[4-trifluoromethoxyphenoxy]pyridine, 4-[4-methylphenoxy]pyridine, 4-phenoxypyridine, 4-[4-methoxyphenoxy]pyridine and/or 4-[2-trifluoromethoxyphenoxy]pyridine.

In a further particularly preferred embodiment, the compounds of the formula (I) are 4-[4-trifluoromethoxyphenoxy]piperidine, 4-[4-methylphenoxy]piperidine, 4-phenoxypiperidine, 4-[4-methoxyphenoxy]piperidine, 4-[2-trifluoromethoxyphenoxy]piperidine, 4-[4-trifluoromethoxyphenoxy]-N-piperidinylacetamide, 4-[4-methylphenoxy]-N-piperidinylacetamide, 4-phenoxy-N-piperidinylacetamide, 4-[4-methoxyphenoxy]-N-piperidinylacetamide and/or 4-[2-trifluoromethoxyphenoxy]-N-piperidinylacetamide.

In a further preferred embodiment of the invention, —C(═O)(R) is an aryl radical.

The scope of the invention encompasses all radical definitions, parameters and illustrations above and listed hereinbelow, specified in general or within areas of preference, in any combination with one another, i.e. also between the particular areas and areas of preference.

Solvents which can be used for the purposes of the invention are organic, polar solvents, aliphatic or alicyclic ketones, ethers, esters, anhydrides, carboxylic acids, alcohols and/or water. In one preferred embodiment of the process according to the invention, the organic polar solvent is aliphatic or alicyclic ketones, ethers, anhydrides, esters and/or mono-, di- or tricarboxylic acids.

The organic, polar solvents are particularly preferably formic acid, acetic acid, propionic acid, n-, t-, isobutanoic acid, isopropanoic acid, pentanoic acid, butanedioic acid, oxalic acid, citric acid, pyrrolidine-2-carboxylic acid or mixtures of these acids.

The organic, polar solvents are very particularly preferably formic acid, acetic acid or propionic acid or mixtures of these acids.

In a further preferred embodiment of the invention, the transition metal of the transition metal catalyst is rhodium, ruthenium, iridium, platinum or palladium and salts thereof, particularly preferably rhodium, ruthenium, platinum or palladium and salts thereof.

In another embodiment of the process according to the invention, the transition metal is preferably located on a support, selected from the group silicon dioxide, aluminium oxide, titanium dioxide, zeolites or carbon. The support is very particularly preferably activated carbon or titanium dioxide.

In the cases where the transition metal catalysts are inorganically supported catalysts, Ru-titanium dioxide, Ru-silicon dioxide, Ru-aluminium dioxide, Ru-carbon, Pd-carbon, Pd-titanium dioxide, Pd-silicon dioxide, Pd-aluminium dioxide, Rh-titanium dioxide, Rh-silicon dioxide, Rh-carbon, ft-carbon, Ir-titanium dioxide, Pt-carbon, Pt-titanium dioxide, Pt-aluminium oxide and/or Pt-silicon dioxide are preferred. Very particularly preferred transition metal catalysts are Pd-carbon, Pd-titanium dioxide, Pd-silicon dioxide, Pd-aluminium dioxide, Pt-carbon, Rh-carbon and Ru-carbon; Pd-activated carbon or Pt-activated carbon are very particularly preferably used.

The transition metal catalysts can be used, for example, as macroscopic solids or as particles, e.g. in the form of a colloidal solution. For example and preferably, the transition metal catalysts have a water content of 1-90%, particularly preferably of 20-80% and very particularly preferably of 40-60%.

The supported or unsupported transition metal catalysts used are standard commercial products.

In the process according to the invention, the hydrogen can be introduced into the reaction mixture, for example, in elemental form. However, the hydrogen can also be produced in situ from other hydrogen sources, such as, for example, hydrazine, hydrogen peroxide, lithium alanate or sodium borohydride. Preference is given to generating the hydrogen outside of the reaction mixture and introducing it.

Many of the compounds of the formula (II) are commercially available. The preparation of the compounds of the formula (II) can take place in accordance with analogous processes known from the prior art and is known to the average person skilled in the art.

However, for example and preferably, the preparation of the compounds of the formula (II) can also take place such that a compound of the formula (III)

(ARYL—N)—Y          (III)

where ARYL-N has the meaning given above and Y is bromine, chlorine, iodine or pseudo-halogen,
is reacted with compounds of the formula (IV)

[R²—O⁻]Cat⁺          (IV)

where Cat⁺ is any desired singly charged cation or a 1/nth equivalent of an n-valent cation, and R² has the meaning given above, Examples of compounds of the formula (IV) are sodium [2-trifluoromethoxyphenolate, sodium trifluoromethylphenolate, sodium 4-trifluoromethoxyphenolate and potassium 4-trifluoromethylphenolate.

Within the context of the invention, pseudohalogen refers to radicals whose chemical properties are highly similar to those of the halogens. These are e.g. sulfonates and halosulfonates, such as e.g. tosylate, triflate, mesylate and nonafluorobutylsulfonate, but also thiocyanate and azide, where halogen has the meaning given above.

In one embodiment of the invention, the concentration of the transition metal in the transition metal catalysts, based on the mass of the compounds of the formula (II) used, is between 0.01 and 10% by weight. Preferably, the concentration is between 1 and 7% by weight. It is particularly preferably between 2 and 5% by weight.

The amount of transition metal catalysts used can be chosen so that the amount of transition metal, based on the compounds of the formula (II), is between 0.0001 and 95 mol %, preferably between 0.001 and 10 mol % and particularly preferably between 0.002 and 1 mol %.

For example and preferably, the quantitative amount ratio of the compounds of the formula (II) and of the organic, polar solvents in the reaction mixture is between 1:2 and 1:1000. Preferably, the quantitative amount ratio is between 1:5 and 1:80. It is particularly preferably between 1:10 and 1:40.

The reaction temperature is preferably between 20° C. and 200° C., particularly preferably between 50° C. and 150° C., very particularly preferably between 70° C. and 100° C.

The reaction is preferably carried out at pressures between 1 and 200 bar, particularly preferably between 20 and 80 bar, very particularly preferably between 30 and 50 bar.

In one embodiment of the invention, firstly the compound of the formula (II) is brought into contact with the organic, polar solvents and then the transition metal catalyst is added. It is also likewise possible to add the transition metal catalysts to the reaction mixture immediately.

The reaction is preferably carried out in an autoclave. Furthermore, it is preferred to work under inert conditions. The inertization can be carried out e.g. by continuously or discontinuously passing inert gases, such as e.g. argon and nitrogen, through the reaction mixture. In this case, hydrogen is then injected in and the mixture is hydrogenated e.g. to constant pressure. However, the reaction can also likewise be ended earlier, thereby producing partially hydrogenated products.

In a particularly preferred embodiment, the compound of the formula (II) is brought into contact with the solvents, in particular the mono- di- or tricarboxylic acids. Afterwards, the transition metal catalysts are added, the autoclave or the reaction mixture is rendered inert, the reaction mixture is heated and only in the last stage is hydrogen injected in and the mixture hydrogenated to constant pressure.

In the manner according to the invention, the compounds of the formula (I) can be prepared in a very short time, i.e. very economically in high yields in industrial processes. The work-up can take place in a manner known per se, e.g. by extraction with known solvents, such as, for example, sodium hydroxide solution and toluene.

The compounds of the formula (I) prepared according to the invention are suitable in particular as intermediates e.g. for the production of medicaments and agrochemicals.

The examples below serve to illustrate the invention without thereby being limited to these.

EXAMPLES

1. Preparation of 4-[4-trifluoromethoxyphenoxy]piperidine 70 g of 4-(4-trifluoromethoxyphenoxy)pyridine (0.27 mol) were dissolved in 362 g of acetic acid (6.03 mol) and initially introduced into an autoclave. 3.5 g of a 50% water-moist 10% strength palladium on active carbon catalyst (2.5% by weight based on the mass in grams of the 4-(4-trifluoromethoxyphenoxy)pyridine used) were added and the autoclave was rendered inert. The reaction mixture was heated to 90° C. and then hydrogen was injected to 40 bar and the mixture hydrogenated to constant pressure. The reaction mixture was cooled, the autoclave was decompressed and the reaction mixture was removed. The catalyst was filtered over kieselguhr (Celite) and the solvent was removed under reduced pressure. The crude product was taken up in toluene and extracted with sodium hydroxide solution, the phases were separated and the organic phase was evaporated to dryness under reduced pressure.

This gave 50 g of 4-[4-trifluoromethoxyphenoxy]piperidine (0.19 mol) in a yield of 69.8%.

2. Preparation of 4-[4-methoxyphenoxy]-N-piperidinylacetamide 20 g of 4-(4-methoxyphenoxy)pyridine (99 mmol) were dissolved in 400 g of acetic acid (6.66 mol) and initially introduced into an autoclave. 1.6 g of a 50% water-moist 10% strength palladium on active carbon catalyst (4% by weight based on the mass in grams of the 4-(4-methoxyphenoxy)pyridine used) were added and the autoclave was rendered inert. The reaction mixture was heated to 90° C. and then hydrogen was injected to 40 bar and the reaction mixture was hydrogenated to constant pressure. The reaction mixture was cooled, the autoclave was decompressed and the reaction mixture was removed. The solution was filtered off from the catalyst and the solvent was removed under reduced pressure. The crude product was taken up in toluene and extracted with sodium hydroxide solution, the phases were separated and the organic phase was evaporated to dryness under reduced pressure.

This gave 19.8 g of 4-[4-methoxyphenoxyl]-N-piperidinylacetamide (79 mmol) in a yield of 80%.

What is claimed is:

1. A process for the preparation of compounds of the formula (I)

[R²—O]—CYCLYL—N—R¹  (I)

comprising reacting compounds of the formula (II)

[R²—O]—ARYL—N  (II)

in the presence of at least one transition metal catalyst, excluding platinum catalysts,
at least one organic polar solvent
and hydrogen,
wherein CYCLYL-N is an 5- to 8-membered, cyclic saturated or partially unsaturated, nonaromatic N-heterocyclic radical having up to two nitrogen atoms which is linked via a ring carbon atom to the oxygen atom of the R²—O radical, and ARYL-N is an N-heterocyclic 5- to 8-membered aromatic radical having up to two nitrogen atoms which is linked via a ring carbon atom of the aromatic radical to the oxygen atom of the R²—O radical and R² is an $C_6$-$C_{20}$-aryl which is optionally substituted and
R¹ is bonded to a nitrogen atom of the CYCLYL-N and is hydrogen or —C(=O)(R) and R is $C_1$-$C_{15}$-alkyl, $C_1$-$C_8$-alkylthio, $C_1$-$C_8$-alkoxy, $C_6$-$C_{24}$-aryl, $C_8$-$C_{26}$-arylalkyl, $C_1$-$C_8$-haloalkyl, $C_1$-$C_8$-haloalkoxy, $C_1$-$C_8$-haloalkylthio, where halogen=F, Cl, Br, 5- to 8-membered saturated heterocycle where hetero =(oxygen, sulphur, or nitrogen), hydrogen or $C_1$-$C_8$-mono- or $C_1$-$C_{16}$-dialkylamino.

2. A process according to claim 1, wherein said R² $C_6$-$C_{20}$-aryl is substituted with ($C_1$-$C_6$)-alkyl, ($C_1$-$C_6$)-alkoxy, ($C_1$-$C_7$)-perfluoroalkyl, ($C_1$-$C_7$)-perchloroalkyl, ($C_1$-$C_7$)-perfluoroalkoxy and/or ($C_1$-$C_7$)-perchloroalkoxy radical.

3. A process according to claim 1, wherein ARYL-N is pyridyl, pyrimidinyl, imidazolyl and/or pyridazinyl, where these are substituted by ($C_1$-$C_6$)-alkyl, ($C_1$-$C_6$)-alkoxy, ($C_1$-$C_7$)-perfluoroalkyl, ($C_1$-$C_7$)-perchloroalkyl, ($C_1$-$C_7$)-perfluoroalkoxy and/or ($C_1$-$C_7$)-perchloroalkoxy radicals.

4. A process according to claim 1, wherein the organic polar solvent is aliphatic or alicyclic ketones, ethers, anhydrides, esters and/or carboxylic acids.

5. A process according to claim 4, wherein the organic, polar solvents are methanoic acid, ethanoic acid, propanoic acid, n-, t-, isobutanoic acid, isopropanoic acid, pentanoic acid, butanedioic acid, oxalic acid, citric acid and/or pyrrolidine-2-carboxylic acid.

6. A process according to claim 1, wherein the transition metal of the transition metal catalyst is rhodium, ruthenium, and/or palladium.

7. A process according to claim 6, wherein the transition metal catalyst is Ru-titanium dioxide, Ru-silicon dioxide, Ru-aluminium dioxide, Ru-carbon, Pd-carbon, Pd-activated carbon, Pd-titanium dioxide, Pd-silicon dioxide, Pd-aluminium dioxide, Rh-titanium dioxide, Rh-silicon dioxide, Rh-carbon, Ir-carbon, and/or Ir-titanium dioxide.

8. A process according to claim 1, wherein the transition metal is located on a support which consists of silicon dioxide, aluminium oxide, titanium dioxide, zeolite and/or carbon.

9. A process according to claim 1, wherein the compounds of the formula (I) are 4-[4-trifluoromethoxyphenoxy]piperidine, 4-[4-methylphenoxy]piperidine, 4-phenoxypiperidine, 4-[4-methoxyphenoxy]piperidine, 4-[2-trifluoromethoxyphenoxy]piperidine, 4-[4-trifluoromethoxyphenoxy]-N-piperidinylacetamide, 4[4-methylphenoxy]-N-piperidinylacetamide, 4-phenoxy-N-piperidinylacetamide, 4-[4-methoxyphenoxy]-N-piperidinylacetamide and 4-[2-trifluoromethoxyphenoxy]-N-piperidinylacetamide.

10. A process according to claim 1, wherein the hydrogen is produced in situ.

11. A process according to claim 1, wherein the reaction is carried out at a temperature between 20° C. and 200° C.

12. A process according to claim 1, wherein the reaction is carried out at a pressure between 1 and 200 bar.

13. A process according to claim 1, wherein the amount of transition metal, based on the compounds of the formula (II), is between 0.001 and 95 mol %.

14. A process according to claim 1, wherein the quantitative amount ratio of the compounds of the formula (II) to the organic, polar solvent is between 1:5 and 1:80.

* * * * *